United States Patent [19]

Gateau et al.

[11] Patent Number: 5,739,355
[45] Date of Patent: Apr. 14, 1998

[54] PROCESS FOR PRODUCTION OF POLYISOBUTENYLSUCCINIC ANHYDRIDES WITHOUT FORMATION OF RESINS

[75] Inventors: Patrick Gateau; Daniel Binet, both of Maurepas; Jean-Pierre Durand, Chatou, all of France

[73] Assignee: Institut Francais du Petrole, Rueil Malmaison, France

[21] Appl. No.: 601,402

[22] Filed: Feb. 14, 1996

[30]  Foreign Application Priority Data

Feb. 15, 1995 [FR] France .................... 95 01815

[51] Int. Cl.$^6$ .................................. C07D 307/60
[52] U.S. Cl. .................. 549/255; 548/546; 564/204
[58] Field of Search ................................ 549/255

[56]  References Cited

U.S. PATENT DOCUMENTS

| 4,086,251 | 4/1978 | Cengel et al. | 549/255 |
| 4,605,808 | 8/1986 | Samson | 585/525 |
| 5,041,622 | 8/1991 | LeSuer | 560/190 |

FOREIGN PATENT DOCUMENTS

| 43 19 672 | 12/1994 | Germany. |
| 379563 | 4/1973 | U.S.S.R.. |

OTHER PUBLICATIONS

Puskas et. al., J. Polymer Sci. Symposium No. 56, pp. 191–202, 1976.
Danilenko et al., Neftepererab. Neftekhim (Kiev), No. 8, pp. 43–46 (1972).

*Primary Examiner*—Bernard Dentz
*Attorney, Agent, or Firm*—Millen, White, Zelano & Branigan, P.C.

[57]  ABSTRACT

An alkenyl anhydride or polyalkenylsuccinic anhydride is prepared without forming resins, by an ene-synthesis reaction between an olefin or a polyolefin and a maleic anhydride, optionally substituted by one or two methyl groups, in an aromatic solvent that is selected from toluene and xylenes, whereby said anhydride is used at a ratio of 30 to 60% by weight relative to the reaction medium.

More particularly, polyisobutenylsuccinic anhydrides which can be used to form, by reaction with polyethylene polyamines, compositions that contain polyisobutenylsuccinimides, used as detergent additives for motor fuels or as ashless dispersants for motor oils, are produced.

19 Claims, No Drawings

PROCESS FOR PRODUCTION OF POLYISOBUTENYLSUCCINIC ANHYDRIDES WITHOUT FORMATION OF RESINS

BACKGROUND OF THE INVENTION

This invention relates to a process for production of alkenyl anhydrides or polyalkenylsuccinic anhydrides that are free of chlorine.

In the area of additives for petroleum products, particularly detergent additives for motor fuels and dispersants for motor oils, polyisobutenes that are functionalized most often with the aid of maleic anhydride are often used to synthesize the amphophilic compounds that are desired in these applications. These polyisobutenylsuccinic anhydrides are prepared according to two main processes.

The first consists in condensing maleic anhydride on polyisobutene according to an ene-synthesis reaction. This reaction requires a high temperature and reaction times such that, under these conditions, resins that result from the polymerization of the maleic anhydride are produced. These by-products require a filtration stage, which is made very delicate by the consistency of these products. Improvements aimed at reducing the amount of resins are often proposed. They most often involve carrying out the reaction in the presence of inhibitors of radical polymerization, as in documents DE-A-1 102 142, DE-A-3 320 468 and U.S. Pat. No. 3,476,774; halogenated compounds as in documents GB-A-1 356 802, GB-A 1 480 453 (=FR-A-2 273 014), U.S. Pat. No. 3,960,900, DE-A-3 320 468 already cited, U.S. Pat. No. 4,278,604, and U.S. Pat. No. 4,255,340; metallic salts, as in documents GB-A-2 081 274 and WO-82/00467; or peroxides as in document U.S. Pat. No. 4,599,432 (=FR-A-2 555 595). Another method, which is described in, for example, document U.S. Pat. No. 4,496,746, involves causing the maleic anhydride emulsion to react in an inert solvent by virtue of the use of a surfactant. In all cases, the by-products are never totally eliminated.

In a second type of process, first chlorination of polyisobutene is carried out, followed by the condensation of chlorinated polyisobutene and maleic anhydride. This process is competitive with the preceding one owing to a reduction in the reaction temperature, better conversion, and the absence of secondary reactions that lead to insoluble resins. This process, however, usually leads to products that contain a certain amount of residual chlorine, which excludes them from a number of increasingly important applications, in view of the increasingly stringent requirements regarding the chlorine content of additives for petroleum products.

SUMMARY OF THE INVENTION

This invention proposes a process for producing alkenyl anhydrides or polyalkenylsuccinic anhydrides that are free of chlorine, which does not employ an emulsion reaction or a suspension reaction and in which by-products are totally eliminated. This process thus avoids a long, delicate, and costly filtration stage during the preparation of additives for petroleum products that are free of chlorine, particularly detergent additives for motor fuels and ashless dispersants for motor oils.

The process for producing alkenyl anhydrides or polyalkenylsuccinic anhydrides according to the invention comprises the reaction under conditions of ene-synthesis between an olefin or a polyolefin and an unsaturated dicarboxylic anhydride, and in solution in at least one aromatic solvent that is selected from toluene and xylenes.

The olefins and polyolefins that are used can have an average molecular weight in numbers of between 400 and 10,000 and preferably between 400 and 3,000. The polyolefins in question consist more particularly of polyisobutenes that have a content of external double bonds of more than 50%. They are obtained preferably by polymerization of isobutene in the presence of a catalyst that does not contain chlorine, such as, for example, boron trifluoride. The unsaturated carboxylic anhydride is selected more particularly from the group that is formed by maleic anhydride and the maleic anhydrides that are substituted by one or two groups that are methylated on the carbon atoms of the ethylenic bond, namely citraconic anhydride (maleic methyl) and pyrocinchonic anhydride (maleic dimethyl). Preferably, maleic anhydride is used.

An important characteristic of the process of the invention is the use of the reaction of ene-synthesis in an aromatic solvent that is selected from toluene and xylenes. The content of solvent is more particularly between 30 and 60% by weight, for example, 50% by weight of the reaction medium.

Furthermore, the reaction is carried out at a temperature of between 150° and 300° C., preferably between 180° and 250° C., for example, under autogenous pressure. In general, the pressure that is developed during the reaction is between 2 and 40 bars, more particularly between 3 and 10 bars.

The maleic anhydride or substituted maleic anhydride is generally used at a molar ratio of 0.5 to 2, preferably of 1 to 1.2, relative to the olefin or to the polyolefin (most often the polyisobutene).

The alkenyl anhydrides and polyalkenylsuccinic anhydrides (in particular polyisobutenylsuccinic anhydrides) are obtained by the process of the invention with high yields, which can reach 85%. By way of example, in the case of polyisobutenylsuccinic anhydrides that are derived from polyisobutene with a molecular weight of about 1000, such yields correspond to anhydride indices of up to about 0.08 mol of anhydride per 100 g of product.

The alkenylsuccinic anhydrides and polyalkenylsuccinic anhydrides, in particular polyisobutenylsuccinic anhydrides that are obtained by the process of the invention, are intermediate products for the production of detergent additives for motor fuels or ashless dispersants for motor oils.

For this production, the anhydrides are modified, in a known manner, particularly by reaction with amines to form imides.

The amines that are used are more particularly polyethylene polyamines, such as triethylene tetramine, or tetraethylene pentamine, used at, for example, a molar ratio of 0.5 to 1 relative to the alkenyl anhydride—or polyalkenylsuccinic anhydride (in particular polyisobutenylsuccinic anhydride).

The following examples illustrate the invention; preparation examples 1, 5, 7 and 8 are given by way of comparison.

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding French Application No. 95/01815, filed Feb. 15, 1995 is hereby incorporated by reference.

EXAMPLES

Example 1 (Comparative)

Into an autoclave equipped with a stirring system, there is introduced:

250 g of polyisobutene with an average molecular weight in number of close to 1000 and whose composition of double terminal bonds, as determined by NMR [nuclear magnetic resonance] of the proton, is as follows:
90% of external double bonds;
10% of internal double bonds;
and 24.5 g of maleic anhydride.

The mixture is degassed by nitrogen scavenging at room temperature. It is then stirred for 16 hours at 200° C. The unreacted maleic anhydride is then eliminated by distillation under a vacuum at 150° C. After dilution in 275 g of toluene, the reaction mixture is filtered to separate the by-products formed which, once dried, represent 0.55 g or 0.2% by weight of the products used. The toluene is eliminated by distillation under vacuum to produce a product whose anhydride index (number of mols of anhydride per 100 g of product) is 0.071.

Example 2

Into an autoclave equipped with a stirring system, there is introduced:
250 g of polyisobutene with an average molecular weight in numbers of close to 1000 and whose composition of double terminal bonds, as determined by NMR of the proton, is as follows:
90% of external double bonds;
10% of internal double bonds;
and 24.5 g of maleic anhydride
and 147.8 g of xylenes, or 35% by weight of reaction medium.

The mixture is degassed by nitrogen scavenging at room temperature. It is then stirred for 15 hours at 200° C. The pressure that is developed during the reaction is 2.2 bars. No by-product is formed. The unreacted xylenes and maleic anhydrides are eliminated by distillation under vacuum at 150° C. The anhydride index of the product obtained (number of mols of anhydride per 100 g of product) is 0.067.

Example 3

If, in Example 1, all other things being equal, the reaction is carried out in the presence of 274.5 g of xylenes, or 50% by weight of the reaction medium, no by-product is formed. The pressure that is developed during the reaction is 3 bars. After distillation of the xylenes and elimination of the free maleic anhydride under a vacuum at 150° C, a product that has an anhydride index of 0.065 is obtained.

Example 4

If, in Example 3, the reaction temperature is brought to 220° C., no resin formation is noted. The pressure that is developed during the reaction is then 5 bars. The product that is obtained has an anhydride index of 0.075.

Example 5 (Comparative)

If, in Example 1, all other things being equal, the reaction is carried out in the presence of 91.5 g of xylenes, or 25% by weight of the reaction medium, the formation of oily and brown by-products is noted. The presence of these insoluble products means the product cannot be put to any use without purification.

Example 6

If, in Example 3, the xylenes are replaced by an equivalent amount of toluene, the pressure that is reached during the reaction is 6.2 bars, and no by-product is formed. The product that is obtained after distillation of the solvent and elimination of the unreacted maleic anhydride under a vacuum has an anhydride index of 0.067.

Example 7 (Comparative)

If, in Example 3, all other things being equal, the xylenes are replaced by an aromatic cut having an initial distillation point of 186° C. and a final point of 214° C., the product that is obtained, after elimination of the solvent and the unreacted maleic anhydrides under a vacuum, contains 0.3% by weight of insoluble compounds whose infra-red analysis shows acid and aromatic traits. After elimination of the insoluble compounds, the product has an anhydride index of 0.044.

Example 8 (Comparative)

109.6 g of the aromatic cut that is used in Example 5 and 9.6 g of tetraethylene pentamine are added to 100 g of the product that is obtained in Example 1 after filtration and elimination of toluene. The reaction mixture that is thus obtained is stirred for 6 hours at 165° C. The mixture that is obtained has a nitrogen content of 1.8% by weight.

Example 9

110.1 g of the aromatic cut that is used in Example 5 and 10.1 g of tetraethylene pentamine are added to 100 g of the product that is obtained in Example 3. The reaction mixture thus obtained is stirred for 6 hours at 165° C. The final product has a nitrogen content of 1.65% by weight.

To evaluate the performance of a product that is synthesized according to the invention, compared with those of a product coming from a standard ene-synthesis, two series of engine tests (diesel engines and gasoline engines) are carried out.

Example 10

Test on a Diesel Engine

A clogging test of the injectors on an XUD9 engine is carried out. The fuel that is used is a gas oil whose characteristics are presented in detail in Table 1. The tendency toward clogging is determined from the average residual flow of the four injectors, obtained after 6 hours of engine operation. The tests are carried out compared to gas oil alone, while adding the latter with 350 ppm of the solutions that are obtained in Examples 8 and 9 (or 250 ppm of active material).

TABLE 1

| Density | 837.2 kg/m$^3$ |
|---|---|
| Sulfur content | 0.045% by weight |
| Distillation | |
| Initial point | 204.5° C. |
| 5% | 240.0° C. |
| 10% | 253.0° C. |
| 20% | 269.5° C. |
| 30% | 280.5° C. |
| 40% | 287.5° C. |
| 50% | 293.0° C. |
| 60% | 298.0° C. |
| 70% | 303.5° C. |
| 80% | 309.5° C. |
| 90% | 321.0° C. |
| 95% | 336.5° C. |
| Final point | 349.0° C. |

The results are summarized in Table 2 and show the effectiveness of the products according to the invention compared to those obtained from standard ene-synthesis.

TABLE 2

Injectors Clogging Results
(XUD9 - 6 hours)

| Length of stroke of the needle (mm) Average residual flow (%) | 0.1 | 0.2 | 0.3 |
|---|---|---|---|
| Gas oil (reference) | 14.7 | 23.9 | 33.4 |
| Gas oil + 500 ppm of additive of Example 8 | 31.2 | 41.1 | 51.7 |
| Gas oil + 500 ppm of additive of Example 9 | 36.4 | 47.2 | 57.6 |

Example 11

Test of a gasoline engine

Formulations based on the additives of Examples 8 and 9 and 50 parts of polypropylene glycol with a molecular weight of close to 1000 are prepared. Engine tests are carried out to evaluate the effect of additives on the amounts of deposits at the intake valves.

The test method employs a Mercedes M 102 E engine, run on a 60 hour programmed cycle of stops and starts. The reference fuel used is an unleaded fuel that has a "research" octane number of 96.8. The tests are conducted in the presence of 750 ppm of formulations to be tested and compared to a test with no additive. The results that are obtained (Table 3) are expressed in terms of weight (in grams) of deposits on the annular intake valves. They show the effectiveness of an additive as proposed by the invention compared to the effectiveness of a product that is obtained from a Polyisobutenylsuccinic anhydride that is prepared according to a standard method.

TABLE 3

M 102 E Test - Amounts of Deposits (in Grams)

| Content (in ppm) | Without additive 0 | Additive of Example 8 750 | Additive of Example 9 750 |
|---|---|---|---|
| Valve 1 | 0.312 | 0.152 | 0.126 |
| Valve 2 | 0.348 | 0.095 | 0.052 |
| Valve 3 | 0.256 | 0.070 | <0.001 |
| Valve 4 | 0.195 | 0.009 | 0.007 |
| Total | 1.111 | 0.326 | 0.185 |
| Average deposit/ valve (g) | 0.278 | 0.082 | 0.046 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process comprising contacting under ene-synthesis reaction conditions at least one polyisobutene having a content of external double bonds that is greater than 50%, with at least one unsaturated dicarboxylic anhydride which is maleic anhydride or maleic anhydride substituted by 1 or 2 methyl groups, in at least one aromatic solvent that is toluene or a xylene; said aromatic solvent being employed at a ratio of 35 to 60% by weight relative to the reaction medium, whereby a polyisobutenylsuccinic anhydride is produced.

2. A process according to claim 1, wherein said olefin or polyolefin has a number average molecular weight of 400 to 10,000.

3. A process according to claim 1, wherein said olefin or polyolefin has a number average molecular weight of 400 to 3000.

4. A process according to claim 1, wherein the reaction is carried out at a temperature of 150° to 300° C.

5. A process according to claim 1, wherein the reaction is carried out at a temperature of 180° to 250° C.

6. A process according to claim 1, wherein the maleic anhydride or substituted maleic anhydride is used in a molar ratio of 0.5 to 2 with respect to the olefin or the polyolefin.

7. A process according to claim 1, further comprising reacting said polyisobutenylsuccinic anhydride with an amine, whereby an imide is formed.

8. A process according to claim 7, wherein the imide is produced by the reaction of at least one polyisobutenylsuccinic anhydride with at least one polyethylene polyamine.

9. A process according to claim 8, wherein the polyethylene polyamine is used at a molar ratio of 0.5 to 1 relative to the polyisobutenylsuccinic anhydride.

10. An polyisobutenylsuccinic anhydride that is obtained by a process according to claim 1.

11. A polyisobutenylsuccinic anhydride that is obtained by a process according to claim 1, by reaction between a polyisobutene with a content of external double bonds that is greater than 50% and maleic anhydride.

12. A process according to claim 1, wherein the unsaturated dicarboxylic anhydride is citraconic anhydride.

13. A process according to claim 1, wherein the unsaturated dicarboxylic anhydride is pyrocinchonic anhydride.

14. A process according to claim 1, wherein the unsaturated dicarboxylic anhydride is maleic anhydride.

15. A process according to claim 8, wherein the amine is triethylene tetramine or tetraethylene pentamine.

16. A process according to claim 1, wherein the aromatic solvent is toluene.

17. A process according to claim 1, wherein the aromatic solvent is a xylene.

18. A process comprising contacting under ene-synthesis reaction conditions at a temperature of 180°–250° C., at least one polyisobutene having a content of external double bonds that is greater than 50%, with at least one unsaturated dicarboxylic anhydride which is maleic anhydride or maleic anhydride substituted by 1 or 2 methyl groups, in at least one aromatic solvent that is toluene or a xylene; said aromatic solvent being employed at a ratio of 35 to 60% by weight relative to the reaction medium, whereby a polyisobutenylsuccinic anhydride is produced.

19. A process according to claim 1, wherein the aromatic solvent is employed at a ratio ranging from a first value greater than 50% up to a second value of 60%.

* * * * *

UNITED STATES PATENT AND TRADEMARK OFFICE
CERTIFICATE OF CORRECTION

PATENT NO. : 5,739,355

DATED : April 14, 1998

INVENTOR(S) : Patrick Gateau, et al.

It is certified that error appears in the above-identified patent and that said Letters Patent is hereby corrected as shown below:

Column 6, lines 21, delete "olefin or the polyolefin" and insert -- polyisobutene--.

Signed and Sealed this

Sixteenth Day of February, 1999

Attest:

Attesting Officer

Acting Commissioner of Patents and Trademarks